(12) United States Patent
Peterson et al.

(10) Patent No.: US 9,549,701 B2
(45) Date of Patent: Jan. 24, 2017

(54) DEVICE AND METHOD FOR COLLECTING A BLOOD SAMPLE

(75) Inventors: Bart D. Peterson, Farmington, UT (US); Bryan G. Davis, Sandy, UT (US); Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 709 days.

(21) Appl. No.: 13/185,139

(22) Filed: Jul. 18, 2011

(65) Prior Publication Data

US 2012/0016265 A1    Jan. 19, 2012

Related U.S. Application Data

(60) Provisional application No. 61/365,388, filed on Jul. 19, 2010.

(51) Int. Cl.
*A61B 5/15* (2006.01)
*A61B 5/153* (2006.01)

(52) U.S. Cl.
CPC ....... *A61B 5/150503* (2013.01); *A61B 5/1405* (2013.01); *A61B 5/15* (2013.01); *A61B 5/15003* (2013.01); *A61B 5/153* (2013.01); *A61B 5/15074* (2013.01); *A61B 5/150213* (2013.01); *A61B 5/150389* (2013.01); *A61B 5/150992* (2013.01)

(58) Field of Classification Search
CPC .............. A61M 5/14244; A61M 5/172; A61M 2005/14204; A61M 2205/3331; A61M 5/14248; A61M 5/1452; A61M 5/16804; A61M 5/16854; A61M 2005/14268; A61M 2005/31518; A61M 2205/3368; A61M 2210/0612; A61M 39/223; A61M 39/24; A61M 5/00; A61M 5/1413; A61M 5/142; A61M 5/14216; A61M 5/14224; A61M 5/14566; A61M 5/14586; A61M 5/14593; A61M 5/168; A61M 5/16813; A61M 5/16831; A61M 5/1687
USPC ........... 600/573, 576, 578, 206, 4, 435, 604; 604/158, 168.01, 164.01, 151, 198, 190, 604/309
See application file for complete search history.

(56) References Cited

U.S. PATENT DOCUMENTS

| | | | | |
|---|---|---|---|---|
| 2,673,561 | A | * | 3/1954 | Peterson, Jr. ........ A61B 5/1405 604/216 |
| 3,163,332 | A | * | 12/1964 | Boyle .................. A61G 7/0503 215/383 |
| 3,859,998 | A | | 1/1975 | Thomas et al. |

(Continued)

FOREIGN PATENT DOCUMENTS

| | | |
|---|---|---|
| GB | 2 001 536 A | 2/1979 |
| JP | S58-212455 A | 12/1983 |

(Continued)

*Primary Examiner* — Devin Henson
*Assistant Examiner* — Matthew Kremer
(74) *Attorney, Agent, or Firm* — Jeanne Lukasavage; Craig Metcalf; Kirton McConkie (57) ABSTRACT

A vent plug is disclosed that includes a body having a distal end, a proximal end, and a lumen extending through the distal and proximal ends. A membrane is disposed across the lumen, the membrane being hydrophobic and air permeable. A fluid chamber is formed within the lumen distal the membrane. A distal lumen opening being shaped and sized to retain blood within the lumen until the internal pressure of the lumen increases in response the a finger pressing against a proximal lumen opening.

14 Claims, 9 Drawing Sheets

(56) References Cited

U.S. PATENT DOCUMENTS

| | | | |
|---|---|---|---|
| 4,003,403 A | | 1/1977 | Nehring |
| 4,193,399 A | | 3/1980 | Robinson |
| 4,200,096 A | | 4/1980 | Charvin |
| 4,257,416 A | * | 3/1981 | Prager .................... 604/507 |
| 4,266,559 A | * | 5/1981 | Akhavi .................... 600/579 |
| 4,269,186 A | | 5/1981 | Loveless et al. |
| 4,416,291 A | * | 11/1983 | Kaufman ............ A61B 5/1422 600/576 |
| 4,507,120 A | * | 3/1985 | Paradis ............... A61M 1/0052 137/205 |
| 4,682,980 A | * | 7/1987 | Suzuki .................... 604/122 |
| 4,703,761 A | * | 11/1987 | Rathbone et al. ........... 600/576 |
| 4,703,763 A | * | 11/1987 | McAlister et al. .......... 600/578 |
| 4,765,588 A | | 8/1988 | Atkinson |
| 4,917,671 A | | 4/1990 | Chang |
| 4,935,010 A | | 6/1990 | Cox et al. |
| 5,032,116 A | | 7/1991 | Peterson et al. |
| 5,226,883 A | | 7/1993 | Katsaros et al. |
| 5,242,411 A | | 9/1993 | Yamamoto et al. |
| 5,290,246 A | | 3/1994 | Yamamoto et al. |
| 5,368,029 A | | 11/1994 | Holcombe et al. |
| 5,542,932 A | * | 8/1996 | Daugherty ........ A61M 25/0693 604/168.01 |
| 5,730,123 A | | 3/1998 | Lorenzen et al. |
| 5,947,932 A | | 9/1999 | Desecki et al. |
| 8,066,670 B2 | | 11/2011 | Cluff et al. |
| 8,070,725 B2 | | 12/2011 | Christensen |
| 2002/0179527 A1 | * | 12/2002 | Yao ..................... A61B 5/1405 210/634 |
| 2004/0181192 A1 | | 9/2004 | Cuppy |
| 2005/0273019 A1 | | 12/2005 | Conway et al. |
| 2006/0009713 A1 | | 1/2006 | Flaherty |
| 2006/0149211 A1 | | 7/2006 | Simpson et al. |
| 2006/0178599 A1 | | 8/2006 | Faupel et al. |
| 2007/0043334 A1 | | 2/2007 | Guala |
| 2007/0060840 A1 | * | 3/2007 | Conway .................... 600/576 |
| 2008/0200904 A1 | * | 8/2008 | Cluff .................... A61M 25/00 604/537 |
| 2008/0255473 A1 | | 10/2008 | Dalebout et al. |
| 2008/0287906 A1 | | 11/2008 | Burkholz et al. |
| 2009/0099431 A1 | | 4/2009 | Dalebout et al. |
| 2009/0157007 A1 | | 6/2009 | McKinnon |
| 2011/0009717 A1 | * | 1/2011 | Davis et al. .................. 600/309 |
| 2011/0224610 A1 | * | 9/2011 | Lum ..................... B65B 3/12 604/125 |
| 2011/0224611 A1 | * | 9/2011 | Lum .................. A61M 5/31511 604/125 |
| 2011/0224612 A1 | * | 9/2011 | Lum .................. A61M 5/31511 604/125 |
| 2012/0016213 A1 | | 1/2012 | Burkholz |
| 2012/0016307 A1 | | 1/2012 | Burkholz et al. |

FOREIGN PATENT DOCUMENTS

| | | | | |
|---|---|---|---|---|
| JP | H01-276042 | | 6/1989 | |
| JP | 2003-287479 A | | 10/2003 | |
| WO | WO81/03426 | * | 12/1981 | ............. A61M 5/18 |
| WO | 02/082052 A2 | | 10/2002 | |
| WO | WO 2004/098685 A1 | | 11/2004 | |
| WO | WO 2005/084548 A1 | | 9/2005 | |
| WO | WO 2008/058132 A2 | | 5/2008 | |
| WO | WO 2008/058133 A2 | | 5/2008 | |
| WO | WO 2009/108676 A2 | | 9/2009 | |

* cited by examiner

DEVICE AND METHOD FOR COLLECTING A BLOOD SAMPLE

RELATED APPLICATIONS

This application claims the benefit of U.S. Provisional Application No. 61/365,388 filed Jul. 19, 2010, entitled DISPENSIBLE FLOW CONTROL PLUG UTILIZING COLUMN OF AIR MOVEMENT TO REPETITIVELY DISPENSE DROPS, and is incorporated herein by reference.

BACKGROUND

The present disclosure relates to venting air and blood sampling with vascular access devices. Blood sampling is a common health care procedure involving the withdrawal of at least a drop of blood from a patient. Blood samples are commonly taken from hospitalized, homecare, and emergency room patients either by finger stick, heel stick, or venipuncture. Once collected, blood samples are analyzed via one or more blood test levels.

Blood tests determine the physiological and biochemical states of the patient, such as disease, mineral content, drug effectiveness, and organ function. Blood tests may be performed in a laboratory, a distance away from the location of the patient, or performed at the point of care, near the location of the patient. One example of point of care blood testing is the routine testing of a patient's blood glucose levels. This involves the extraction of blood via a finger stick and the mechanical collection of blood into a diagnostic cartridge. Thereafter the diagnostic cartridge analyzes the blood sample and provides the clinician a reading of the patient's blood glucose level. Other devices are available which analyze blood gas electrolyte levels, lithium levels, ionized calcium levels. Furthermore, some point of care devices identify markers for acute coronary syndrome (ACS) and deep vein thrombosis/pulmonary embolism (DVT/PE).

Despite the rapid advancement in point of care testing and diagnostics, blood sampling techniques have remained relatively unchanged. Blood samples are frequently drawn using hypodermic needles or vacuum tubes coupled to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Furthermore, each device required adds time and cost to the testing process. Accordingly, there is a need for more efficient blood sampling and testing devices and methods.

SUMMARY

The present invention has been developed in response to problems and needs in the art that have not yet been fully resolved by currently available vascular access systems and methods. As described herein, a vent plug can be used to vent an extravascular system as well as collecting a blood sample and later dispensing the blood sample. These vent plugs can thus reduce the number of steps and devices required to perform these procedures, which can decrease the time and cost of these procedures.

In one aspect of the invention, a vent plug comprises a body having a distal end, a proximal end, and a lumen extending through the distal and proximal ends. A membrane is disposed across the lumen and the membrane is hydrophobic and air permeable. A fluid chamber is formed within the lumen distal the membrane. A distal lumen opening is shaped and sized to retain blood within the lumen until the internal pressure of the lumen increases in response to a finger pressing against a proximal lumen opening.

Implementation can include one or more of the following features. The membrane may be coupled to a proximal lumen opening such that a finger pressing against the proximal lumen opening presses against the membrane. The membrane may be biased to bulge proximally. The volume of displacement caused when the membrane is depressed distally is at least 0.05 mL. The membrane may be disposed within the lumen, and the membrane may be dividing the lumen into an air chamber proximal the membrane and a fluid chamber distal the membrane. The body may include a compressible portion on its proximal end. The compressible portion may form a portion of a surface of the air chamber. The distal lumen opening may have an inner perimeter equal to or less than 2.0 mm. The distal lumen opening may be substantially circular and has a diameter between about 0.1 mm to about 0.6 mm. The distal lumen opening may be substantially circular and have a diameter between about 0.2 mm to about 0.3 mm. The fluid chamber may have a volume of at least 0.1 mL.

In another aspect of the invention, a vent plug comprises a body having a distal end, a proximal end, and a lumen extending through the distal and proximal ends. A membrane is disposed across a portion of the lumen within the lumen. The membrane being hydrophobic and air permeable. The membrane dividing the lumen into an air chamber proximal the membrane and a fluid chamber distal the membrane. A distal lumen opening is shaped and sized to retain blood within the fluid chamber until the internal pressure of the lumen increases in response to a finger pressing against a proximal lumen opening.

Implementation can include one or more of the following features. The body may include a compressible portion on its proximal end, and the compressible portion may form part of a surface of the air chamber. The distal lumen opening may have an inner perimeter equal to or less than 2.0 mm. The distal lumen opening may be substantially circular and may have a diameter between about 0.1 mm to about 0.6 mm. The distal lumen opening may be substantially circular and may have a diameter between about 0.2 mm to about 0.3 mm. The fluid chamber may have a volume of at least 0.1 mL.

In another aspect of the invention, a method for collecting blood samples includes disposing a vent plug in a port of an intravenous infusion therapy system. The vent plug has a body with a lumen therethrough. A membrane is disposed across the lumen. The membrane is hydrophobic and air permeable. A distal lumen opening of the vent plug is shaped and sized to retain blood within the lumen until the internal pressure of the lumen increases in response to a finger pressing against a proximal lumen opening. The method also includes venting air from the intravenous infusion therapy system and at least substantially filling the vent plug with blood. The method also includes removing the vent plug from the intravenous infusion therapy system. Lastly, the method includes expelling a volume of blood from the vent plug by pressing a finger distally into the proximal lumen opening of the vent plug.

Implementation of the method can include one or more of the following features. The membrane may be coupled to the proximal lumen opening and is biased to bulge proximally, and expelling a volume of blood may include depressing the membrane distally. The air permeable membrane may divide the lumen into an air chamber proximal the membrane and a fluid chamber distal the membrane, and wherein expelling a volume of blood may include increasing the internal pressure of the air chamber. The body may include a compressible proximal portion, and expelling a volume of blood may include compressing the compressible proximal portion of the body.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The embodiments of the present invention may be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
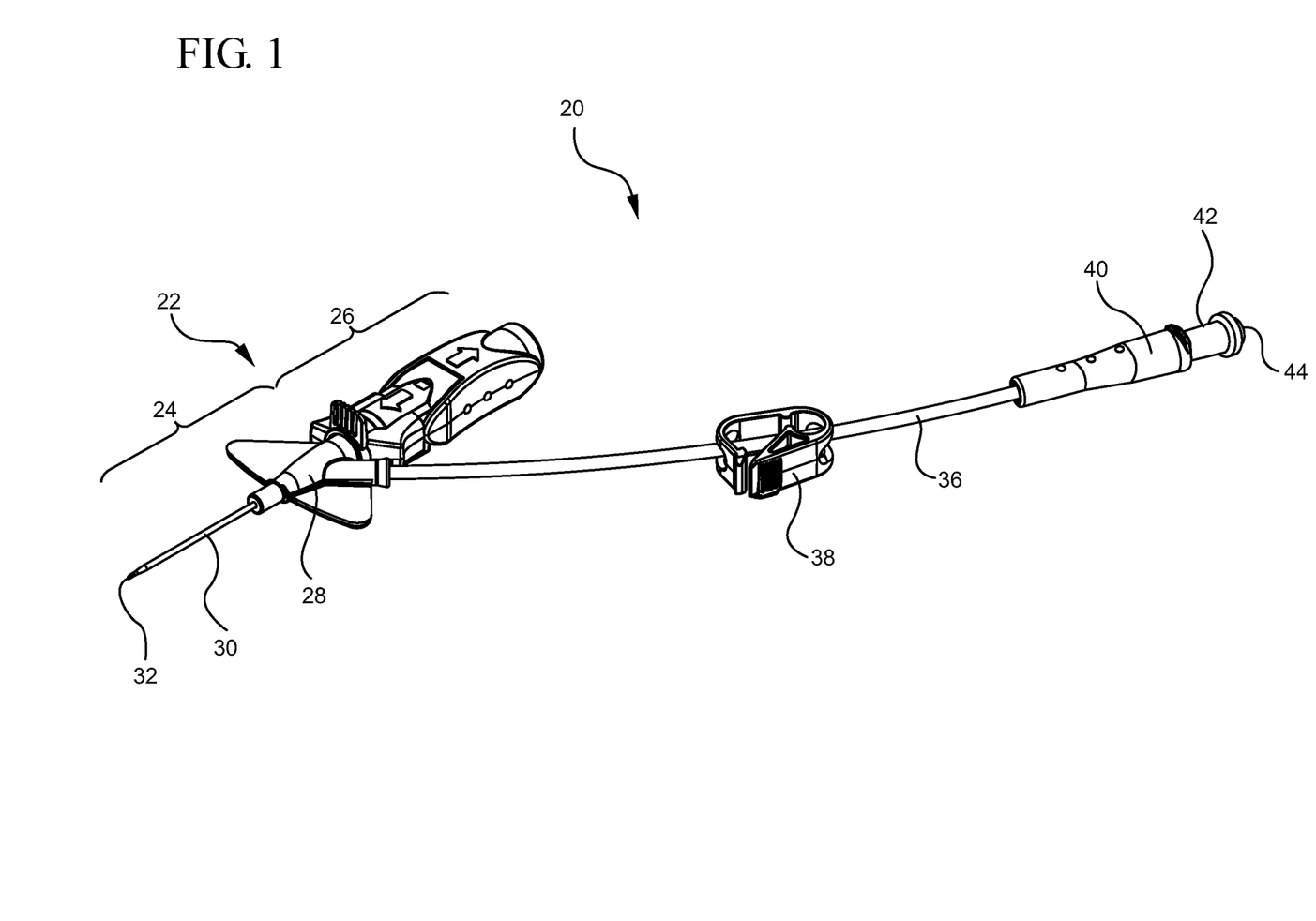
FIG. 1 is a perspective view of an extravascular system with a vent plug, according to some embodiments.

Reference will now be made to FIG. 1, which illustrates an extravascular system with which a vent plug 42 may be used. It will be understood that the vent plug 42 is not limited to the illustrated system, but may be used with other extravascular systems, ranging from a simple needle, to more complex extravascular devices. From this figure it is apparent that a vent plug 42 can, in some configurations, reduce the number of components required to draw a diagnostic blood sample from a patient. This is because the vent plug 42 combines blood venting and blood collecting features into a single device.

FIG. 1 illustrates an extravascular system 20, such as the BD NEXIVA™ Closed Intravenous (IV) Catheter System, by Becton, Dickinson and Company, which can be accessed by a vent plug 42. The illustrated embodiment of the extravascular system 20 includes multiple vascular access devices such as a needle hub 26 coupled to an introducer needle 32 that extends through a catheter assembly 24. The catheter assembly 24 includes a catheter adapter 28 that is coupled to an over-the-needle, peripheral, IV catheter 30 extending therefrom. The introducer needle 32 is left within the catheter assembly 24 until the catheter 30 is inserted into and correctly positioning within the vasculature of a patient, when it is withdrawn. In some embodiments, one or more needle tip shields are incorporated into the needle hub 26 to shield the needle tip after it is removed from the catheter assembly 24.

In some configurations, an integrated extension tubing 36 is coupled to and provides fluid communication with the catheter assembly 24. The extension tubing 36 can also be coupled to a port 40 that provides access to the vascular system of the patient via the extension tubing 36 and the catheter assembly 24. The port 40 can have various configurations, such as a single port Luer adapter, a Y Luer adapter, and other known ports. In some instances, a clamp 38 is used to selectively close the extension tubing 36. As shown, a vent plug 42 can be inserted into the port 40.

While FIG. 1 depicts the vent plug 42 coupled to a port 40 on an extension tubing 36, the vent plug 42 can be coupled to any port 40 in fluid connection to the vasculature of a patient. Such alternative ports could be located on the catheter assembly 24 directly, or more specifically on the catheter adapter 28. In other extravascular system 20, ports 40 can be coupled to a needle, catheter, or other components of the extravascular system 20.

In some embodiments, the vent plug 42 vents air from the catheter assembly 24 and the extension tubing 36 prior to collecting a blood sample therefrom. When the catheter assembly 24 establishes fluid communication with the vasculature of a patient, the internal blood pressure of the vascular system can force blood into the catheter assembly 24 and up into the extension tubing 36. In some instances, it is desirable to permit this blood to fill the catheter assembly 24 and the extension tubing 36 in order to vent air from the extravascular system 20 before fluids are infused through this system into the patient. This process can reduce the likelihood that air is infused into the patient's vasculature. Accordingly, in some embodiments, the vent plug 42 includes a membrane 44 that is air permeable, through which air from within the extravascular system 20 passes. In some embodiments, the membrane 44 is hydrophobic so that it does not permit blood to pass through it. In such embodiments, blood entering the extravascular system 20 forces air out the membrane 44 as it enters the system and fills the system to the membrane 44 of the vent plug 42. At this point, in some instances, the clamp 38 can close the extension tubing 36 while the vent plug 42 is removed and a separate vascular access device, such as an IV line coupled to a fluid reservoir, is coupled to the port 40 to begin an IV therapy process.

As described above, the vent plug 42 includes a membrane 44 that can be both air permeable and hydrophobic, to permit air, but not blood to pass therethrough. The membrane 44 can include various materials and components that provide these properties. For example, in some embodiments, the membrane 44 includes glass, polyethylene terephthalate (PET), a microfiber material, and/or other synthetic material made of high-density polyethylene fibers, such as TYVEK® material from DuPont. Other such materials and components can also be used as a layer of the membrane 44 or as the entire membrane 44 to enable the membrane 44 to be hydrophobic and/or air permeable, according to some configurations.

Figure 2:
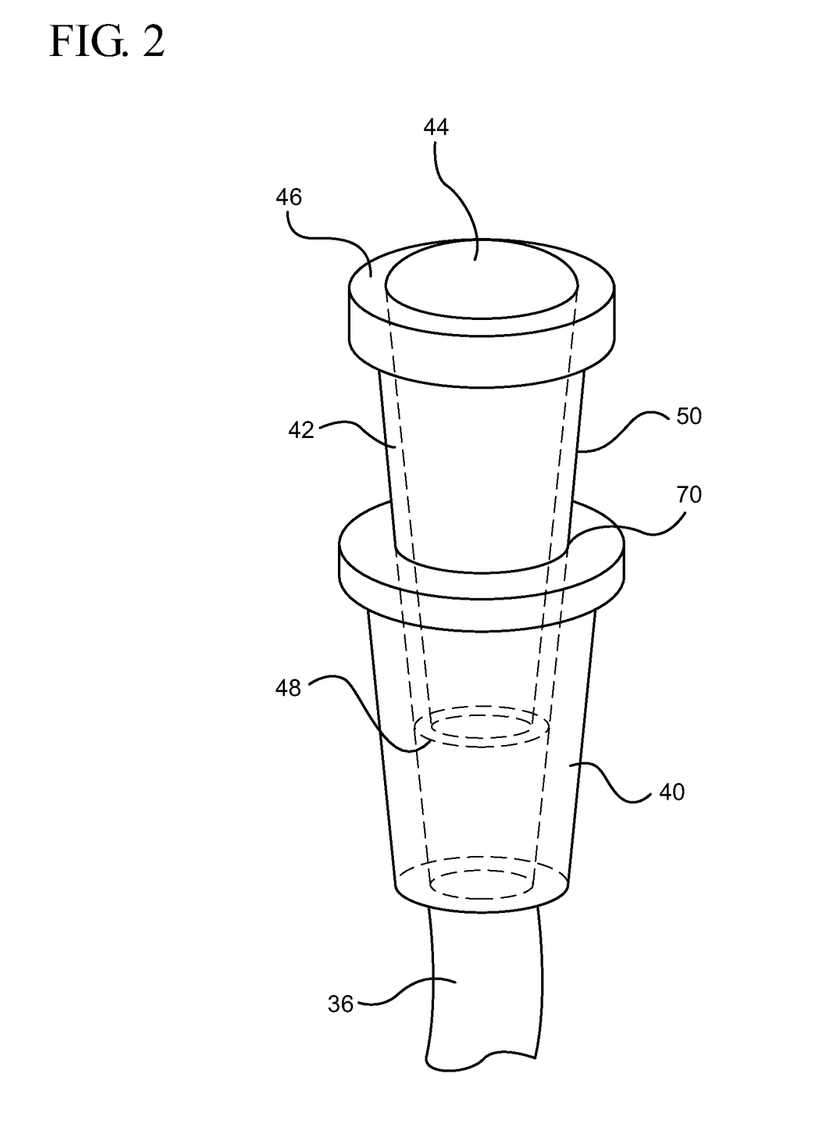
FIG. 2 is a perspective view of a vent plug in a port, according to some embodiments.
Figure 3:
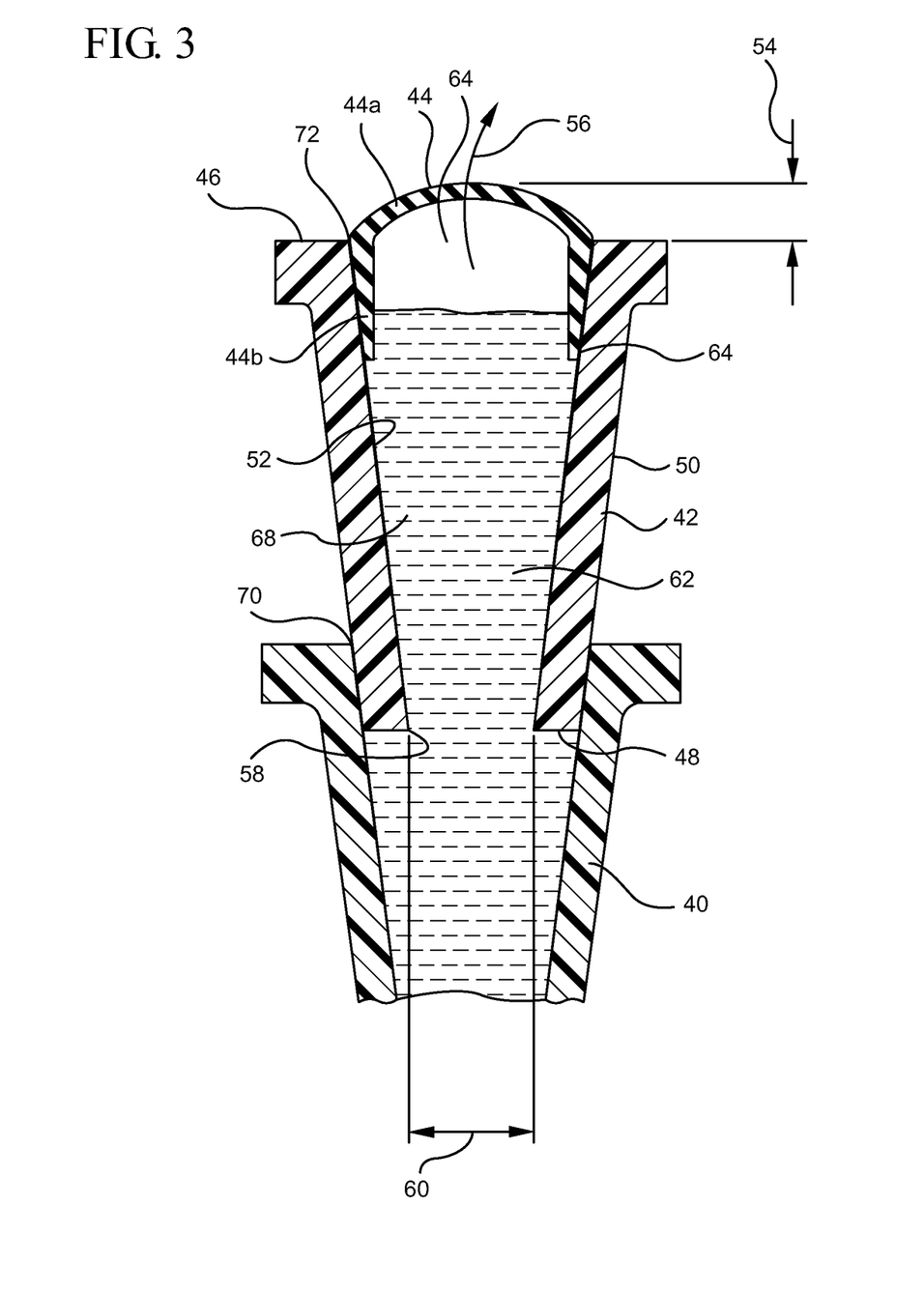
FIG. 3 is a cross section view of the vent plug and port of FIG. 2, according to some embodiments.
Figure 4:
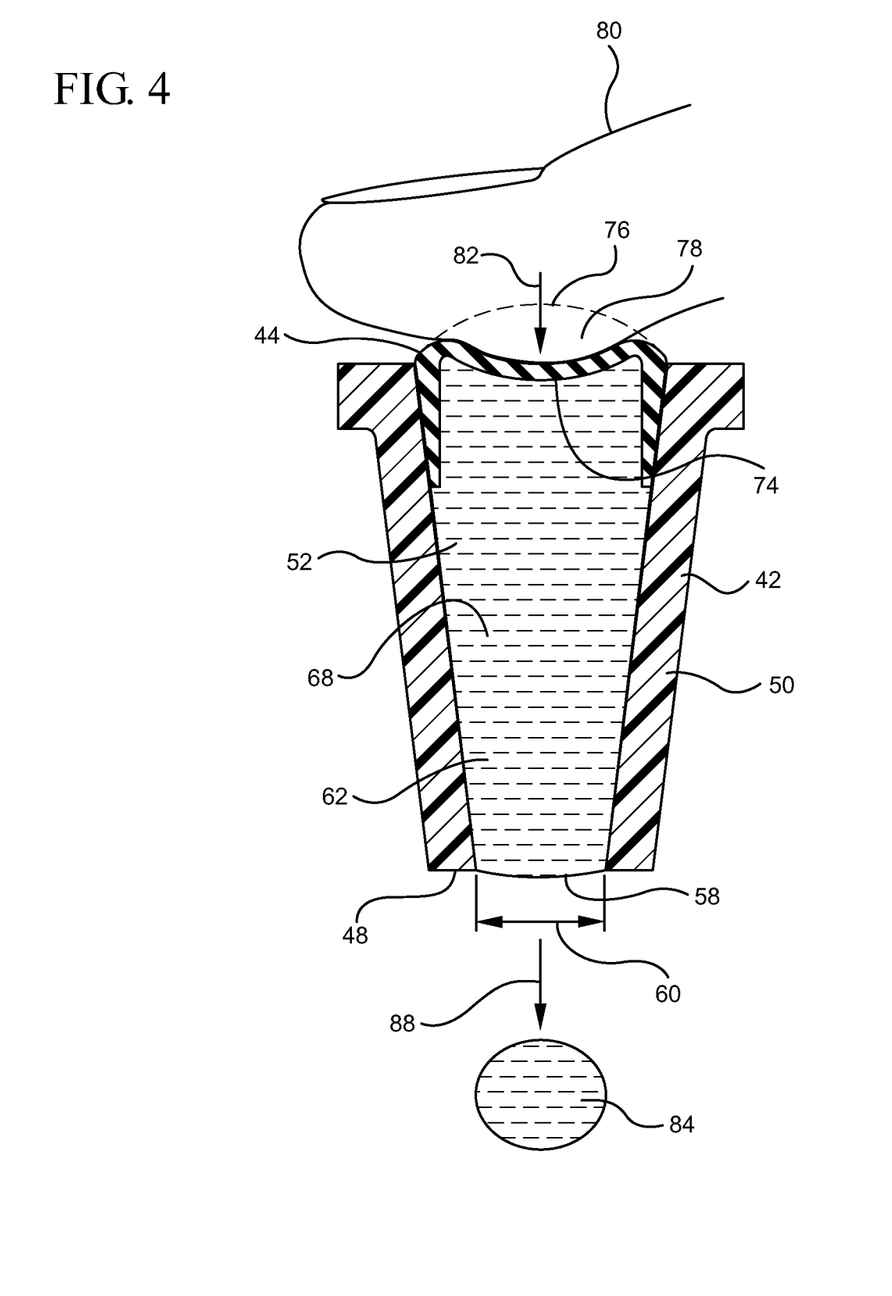
FIG. 4 is a cross section view of the vent plug of FIGS. 2 and 3 following the removal of the vent plug from the port, according to some embodiments.

As illustrated in FIGS. 2 and 3, in additional to venting air 64 from the extravascular system 20, the vent plug 42 can collect a sample of blood 62 therein that can be used for blood testing or other procedures. FIG. 2 illustrates a close-up view of the vent plug 42 inserted into the opening 70 of a port 40 coupled to an extension tube 36, similar to that of FIG. 1, and FIG. 3 illustrates a cross-sectional view of the devices of FIG. 2. As illustrated, the vent plug 42 can include a body 50 that has a lumen 52 extending between the proximal end 46 and the distal end 48 of the body 50. The body 50 can have a variety of shapes and sizes. As shown, the body 50 forms a tapered cylinder, but in other embodiments, the body 50 can have other shapes and sizes. In some embodiments, the membrane 44 is disposed and/or coupled to the proximal lumen opening 72 of the body 50, as shown, creating a fluid chamber 68 within the lumen 52 and distal the membrane 44. The membrane 44 can have coupling portion 44b that is coupled to the body 50 of the vent plug 42. The membrane 44 can have an exposed portion 44a that is biased to bulge proximally, as shown. This exposed portion 44a can bulge outwards a sufficient distance 54 that permits the membrane 44 to be depressed by the average adult finger from the bulged position, or pre-depressed position (element 76 in FIG. 4), to a depressed position (element 74 in FIG. 4), in order to compress the volume of the fluid chamber 68 sufficiently to expel a blood drop 84 therefrom, as described below. In some embodiments, a blood drop is at least 0.05 mL. Accordingly, in some configurations, the membrane 44 is flexible, so that is can be depressed, as shown in FIG. 4.

During venting, as blood 62 is forced into the vent plug 42, air 64 within the lumen 52 is forced through the membrane 44 via one or more air flow paths 56. During this process, a sample of blood 62 can be collected within the fluid chamber 68. The volume of blood collected can be controlled in part by the size of the fluid chamber 68, which can thus be designed to contain the desired volume of blood. Most blood tests require a minimum of about 0.1 µL of blood, accordingly, the fluid chamber 68 can be at least this big. In other embodiments, the fluid chamber 68 is sized to contain up to about 10 mL of blood. In other embodiments, the fluid chamber 68 can be even larger than 10 mL.

In some embodiments, the vent plug 42 can be configured to retain blood 62 as it is withdrawn from the port 40 to prevent blood spills and blood contamination. Thus, in some configurations, the distal lumen opening 58 is shaped and sized to retain blood 62. Blood retention within the lumen 52 is governed, at least in part, by the inner perimeter of the distal lumen opening 58, the surface tension of blood, and the force on the blood 62 to flow out of the distal lumen opening 58. Accordingly, the inner perimeter of the distal lumen opening 58 can be designed so that blood 62 is retained within the fluid chamber 68 when the force of the blood 62 to flow out of the distal lumen opening 58 is within a certain range, but permit at least some blood to flow out when the pressure on the blood 62 exceeds this range.

For example, in some embodiments, when the distal lumen opening 58 is circular, an inner perimeter of less than or equal to approximately 2.0 mm, and a diameter 60 of less than or equal to approximately 0.6 mm, permits the retention of blood within the lumen 52 against approximately the force of gravity. When the force on the blood 62 is greater than the force of gravity some blood 42 can flow out of the distal lumen opening 58. Similarly, a circular distal lumen opening 58 with a diameter of about 0.3 mm may retain blood 62 therein against forces stronger than gravity, such as bumping, jarring, and movement of the filled vent plug 42. When the distal lumen opening 58 has a very small inner perimeter, the force required to expel blood 62 will be very large.

Figure 5:
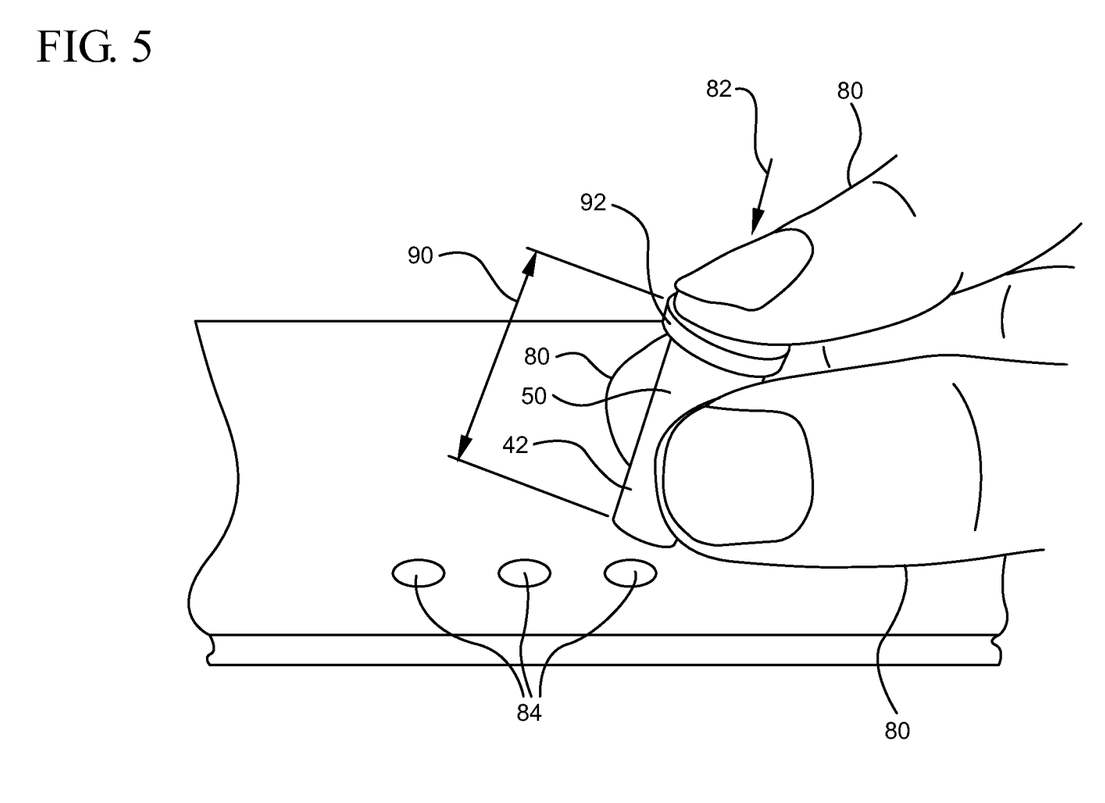
FIG. 5 is a perspective view of fingers gripping a vent plug and expelling blood drops therefrom, according to some embodiments.

As shown in FIGS. 4 and 5, in some embodiments, the vent plug 42 is able to expel blood 62 out of the vent plug 42 after it is withdrawn from a port 40. Referring to FIG. 5 specifically, in some instances, blood 62 collected with the vent plug 42 can be expelled onto a test strip or onto another object for testing purposes when a finger 80 presses against the membrane 44 to increase the pressure within the lumen 52. This process will be described in greater detail below. To facilitate blood expulsion, the distal lumen opening 58 can be configured large enough so that an average adult finger can apply sufficient pressure to expel a blood drop 84 from the fluid chamber 68. Thus, in some embodiments, the distal lumen opening 58 has a inner perimeter greater than or equal to about 0.3 mm, which when the distal lumen opening 58 is a circular opening, corresponds to a diameter of about 0.1 mm. Thus, in some configurations, the distal lumen opening 58 has an inner perimeter between about 0.3 mm to about 2.0 mm. In some configurations, the distal lumen opening 58 is approximately circular and has a diameter between about 0.1 mm to about 0.6 mm. In other embodiments, the distal lumen opening 58 is non-circular.

Reference will now be made to FIG. 4. FIG. 4 illustrates a cross-section view of a vent plug 42 after it is removed from a port 40. Similar to the vent plug 42 illustrated in FIG. 3, a membrane 44 is coupled to a top portion of the body 50 of the vent plug 42. In some embodiments, the membrane 44 is coupled to an inner surface of the inner lumen 52 of the body. This coupling can be mechanical or chemical, for example, using an adhesive or another fastener 64. In other embodiments, the membrane 44 is coupled to a top surface of the body 50 rather than being disposed within the lumen 52.

In some configurations, the membrane 44 is biased to bulge proximally, as shown in FIG. 3. The bulging portion can act as a button that when sufficiently pressed downward 82 may cause one or more blood drops 84 to drop from the fluid chamber 68. As shown in FIG. 4, the bulging nature of the membrane 44 positions the membrane 44 in a pre-depressed position 76 until it is depressed to a depressed position 74 by the downward 82 force of a finger 80. This downward 82 force results in a decrease in the volume of the fluid chamber 68 that is approximately equal to the volume of displacement 78 between the pre-depressed 76 and depressed 74 positions of the membrane 44, as shown. As the volume of the fluid chamber 68 decreases, the pressure within the fluid chamber 68 increases. In some instances, this pressure increase within the fluid chamber 68 causes one or more blood drops 84 to be expelled downward 82 and out of the fluid chamber 68, as shown. After the blood drop 84 is expelled and the pressure of the finger 80 is released, the membrane 44 is permitted to return to its biased pre-depressed position 76. As the membrane 44 moves upward, the volume of the fluid chamber 68 expands decreasing the internal pressure of the fluid chamber 68, drawing air therein. This new air may move upwards as the heavier blood 62 sinks toward the distal lumen opening 58. At this point, the membrane 44 of the vent plug 42 can be depressed again to expel another blood drop 84. Thus, as described, in some embodiments, the vent plug 42 can be selectively activated to release blood drops 84 on command, as shown in FIGS. 4 and 5.

FIG. 5 depicts the action of selectively releasing blood drops 84 from the vent plug 42 onto a surface. As shown, a practitioner can grip the vent plug 42 with one or more fingers 80. Then by sufficiently depressing the membrane 44, the practitioner can expel one or more blood drops 84 from the vent plug 42. In some embodiments, the volume of displacement 78 between the pre-depressed position 76 and the depressed position 74 can be designed to cause the expulsion of two or more blood drops 84 or a single large blood drop 84. Furthermore, in some embodiments, the membrane 44 is configured so that it is capable of being only partially depressed so that a smaller blood drop 84 is expelled than would be if the membrane 44 were completely depressed.

As shown in FIG. 5, in some embodiments, the body 50 of the vent plug 42 is shaped and sizes so that it can be gripped between two or more fingers 80. Accordingly, in some configurations, the length 70 of the body 50 is approximately equal to or greater than the width of the average human thumb. The body 50 can also be wide enough to be adequately gripped within two or more fingers 80. As further shown, in some embodiments, the body 50 includes a top disk 92 or other like structure from which the membrane 44 bulges outward. This top disk 92 can be used to leverage the vent plug 42 out of a port 40 and/or to prevent a finger 80 that is gripping the side of the body 50 from accidentally depressing the membrane 44.

Figure 6:
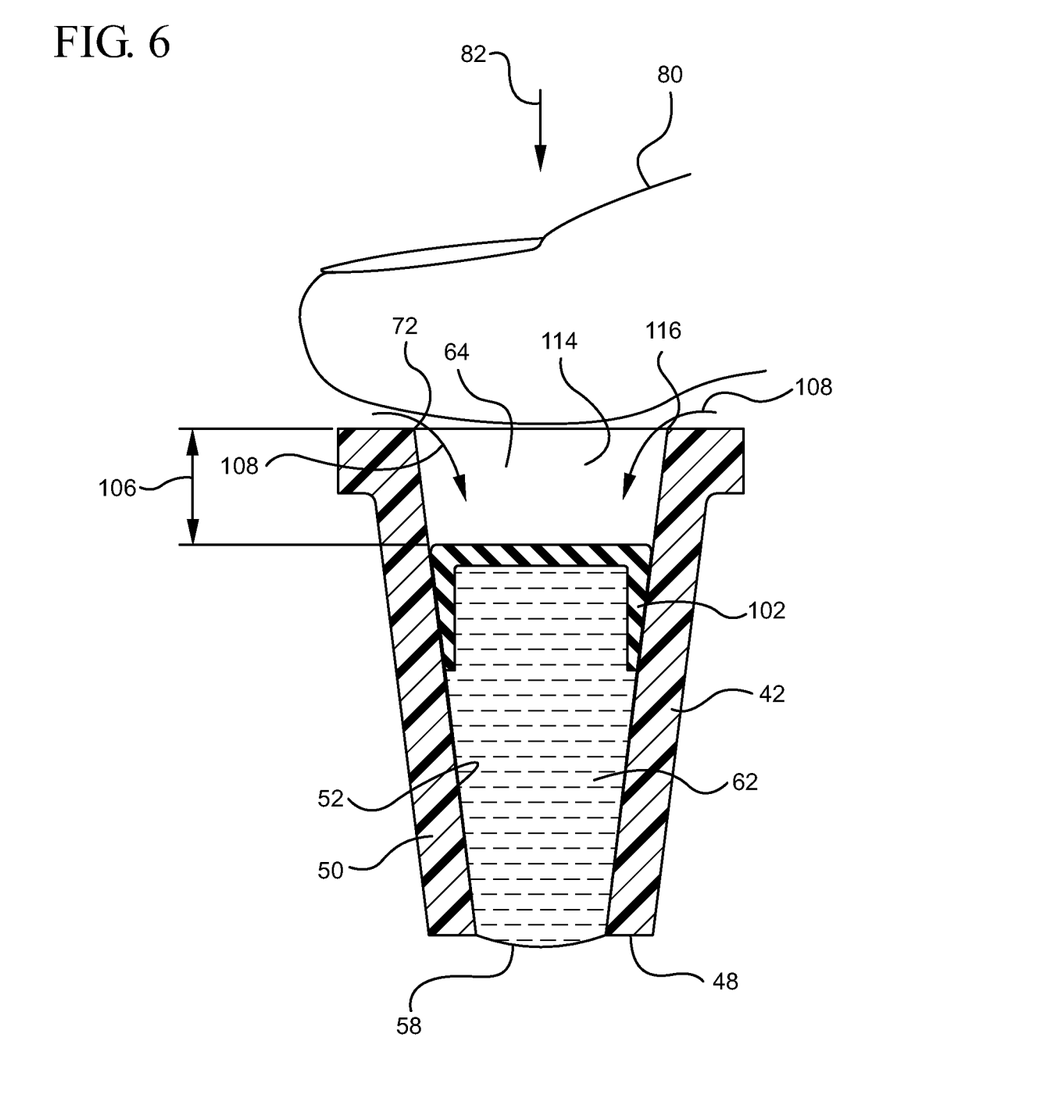
FIG. 6 is a cross section view of another vent plug, according to some embodiments.

FIG. 6 depicts a vent plug 42 having a membrane 102 disposed within the lumen 52. In this position, the membrane 102 divides the lumen 52 into an air chamber 114 proximal the membrane 102 and a fluid chamber 68 distal the membrane 102. Similar to the embodiments of FIGS. 4 and 5, the vent plug 42 of FIGS. 6 and 7 can be capable of expelling one or more drops of blood 84 when a finger 80 is pressed downward 82 against the proximal lumen opening 72 of the body 50. However, different from the embodiments of FIGS. 4 and 5, the vent plug 42 of FIGS. 6 and 7 expels blood 62 as air is forced from the air chamber 114 through the membrane 102 into the fluid chamber 58 rather than in response to the movement of the membrane 102. This increase of air increases the internal pressure inside the fluid chamber, which can cause one or more drops of blood to be expelled out the distal lumen opening 58.

Figure 7:
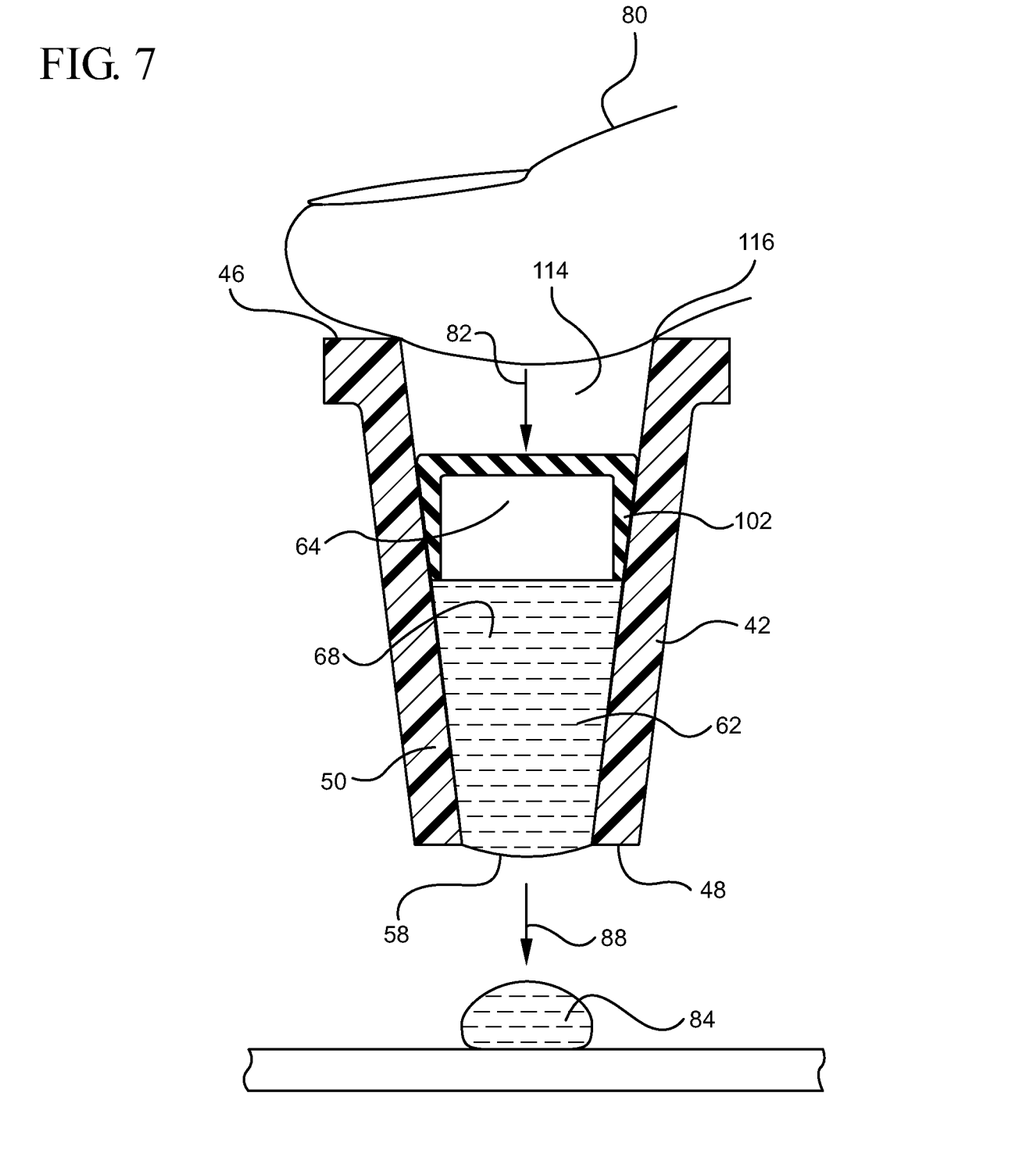
FIG. 7 is a cross section view of the vent plug of FIG. 6, while blood is being expelled therefrom with a finger, according to some embodiments.

In some embodiments, to more effectively expel a blood drop 84, the finger 80 covers the proximal lumen opening 72 to seal this opening. Once sealed, or substantially sealed, the finger 80 can be pressed deeper (distally) into the lumen 52 to compress the air 64 within the air chamber 114. In some configurations, the proximal lumen opening 72 is rounded, to provide more comfort to the practitioner and to facilitate sealing of this opening. Likewise, in other configurations, the proximal lumen opening 72 includes a cushion, such as an elastomeric material disposed thereon. In some embodiments, this cushion can act as a compressible member, as will be described below.

As shown in FIGS. 6 and 7, as a finger 80 is pressed downward 82 against the proximal lumen opening 72, air 64 can enter the air chamber 114 via flow paths 108 between the finger 80 and the body 50 of the vent plug 42. As the finger 80 presses farther against the inner surface 116 of the proximal lumen opening 72 it can at least partially seal the proximal lumen opening 72 and compressed the air 64 within the air chamber 114. The distance 106 between the proximal lumen opening 72 and the membrane 102 can be far enough that the average adult finger 80 does not contact the membrane 102 as the finger 80 is pressed against the proximal lumen opening 72. The compression of air within the air chamber 114 can force air 64 through the membrane 102 into the fluid chamber 68. As this air is introduced into the fluid chamber 68 it increases the pressure in that chamber and can cause one or more blood drops 84 to be expelled out the distal lumen opening 58. Accordingly, in some embodiments, the vent plug 42 can be selectively activated to release blood drops 84 on command, similar to the vent plug 42 depicted in FIG. 5.

Figure 8:
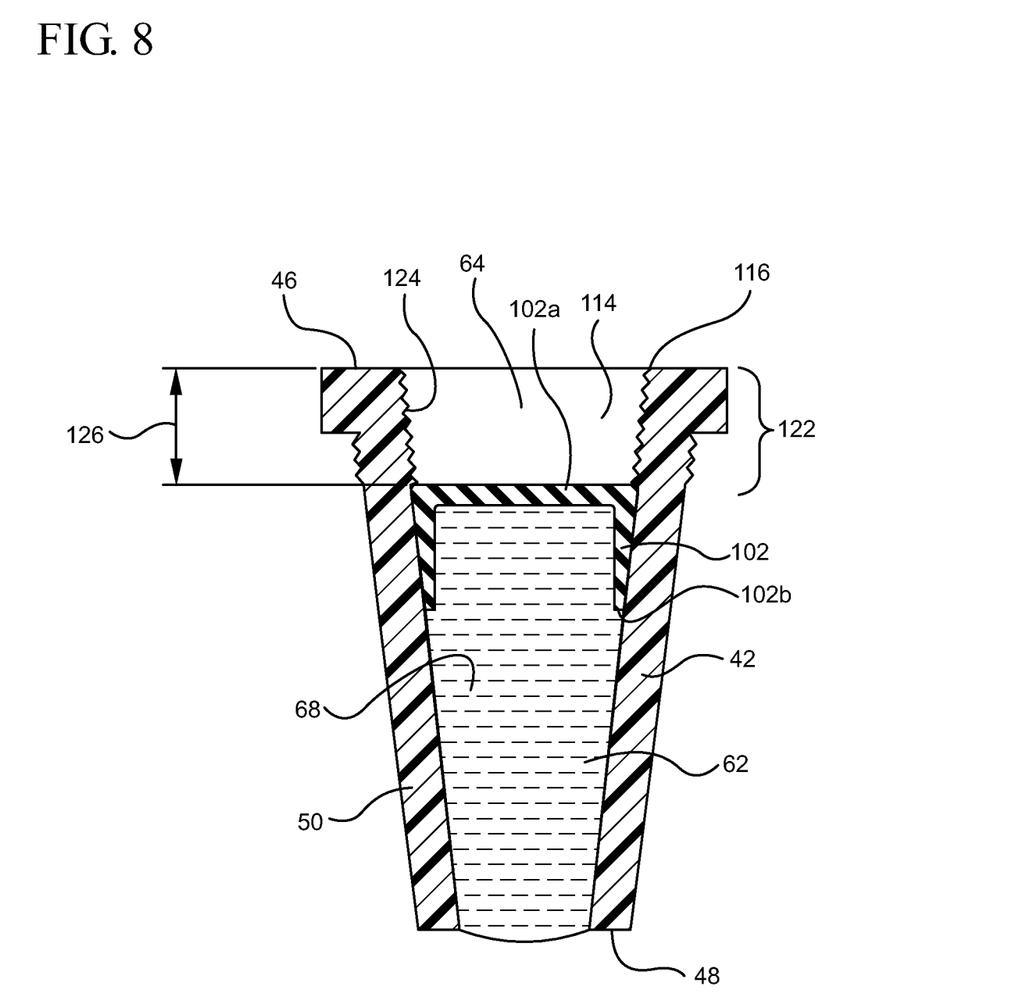
FIG. 8 is a cross section view of another vent plug, according to some embodiments.
Figure 9:
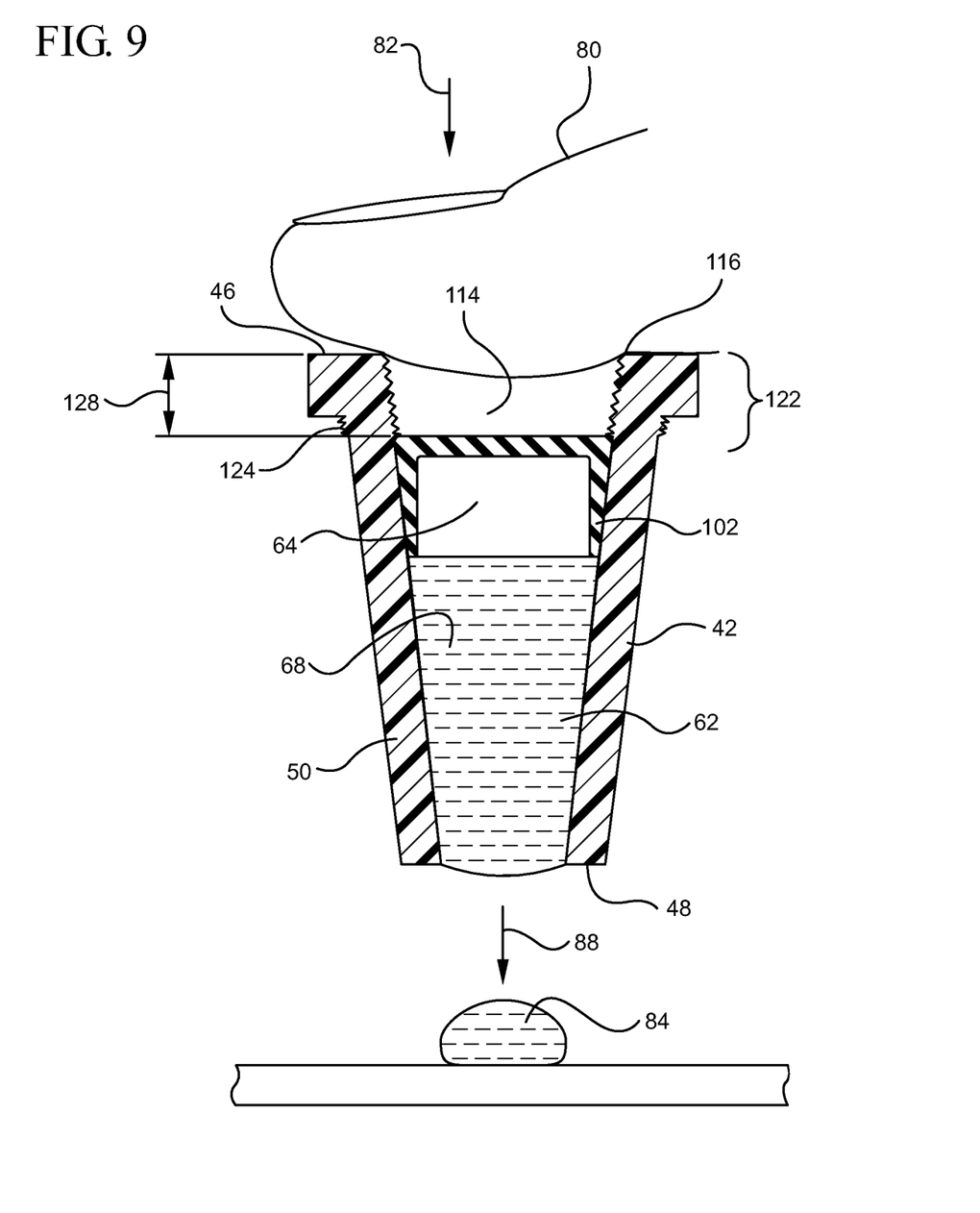
FIG. 9 is a cross section view of the vent plug of FIG. 8, while blood is being expelled therefrom with a finger, according to some embodiments.

FIGS. 8 and 9 illustrate variations to the vent plug 42 shown in FIGS. 6 and 7. As shown, this vent plug 42 includes a compressible portion 122 that forms part of the barrier of the air chamber 114. This compressible portion 122 may include one or more accordion-type member 124 that compressed when a downward (distal) 82 force is applied thereto. Other types of compressible members can include a spring, an elastomer, or another like member. A compressible portion 122 can be made of the same material as the remainder of the body 50 or it can be made of a separate material, for example, as an elastomeric material like a rubber, silicone rubber, etc.

In some embodiments, the vent plug 42 is activated similarly to that of FIGS. 6 and 7, as a finger 80 is pressed against the proximal lumen opening 72. The finger 80 can seal or substantially seal the air chamber 114 and compress the compressible portion 122 of the air chamber 114. The compressible portion 122 can enable additional pressurization of the air chamber 114, causing more air 64 to be forced through the membrane 102 as it compresses the height of the air chamber 114 from an uncompressed height 126 to a compressed height 128. The decrease in height further pressurizes the air chamber 114, providing additional force for forcing air 64 through the membrane 102 and expel one or more blood drops 84 out the distal lumen opening 58, as described above.

From the foregoing, it will be seen that the embodiments of a vent plug 42 described herein can be used to vent an extravascular system 20 as well as collecting a blood sample and later and dispensing the blood sample. Thus, these embodiments of a vent plug 42 reduce the number of steps and devices required to perform these procedures, which can decrease the time and cost of these procedures.

The present invention may be embodied in other specific forms without departing from its structures, methods, and/or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A vent plug comprising:
   a body having a distal terminal end, a proximal terminal end, and a lumen extending from the distal terminal end to the proximal terminal end to form a distal lumen opening at the distal terminal end and a proximal lumen opening at the proximal terminal end;
   a membrane having an inner surface and an outer surface, the membrane being disposed at the proximal terminal end of the body and continuously across an entire width of the proximal lumen opening of the lumen, the membrane configured to prevent passage of blood through the membrane, the membrane being hydrophobic and air permeable, the membrane coupled to the proximal terminal end of the body, the membrane comprising a depressable exposed portion that is biased to bulge proximally out from the proximal lumen opening such that a portion of the inner surface of the membrane is positioned proximal to the proximal lumen opening; and
   a fluid chamber formed within the lumen distal the membrane for collecting the blood, the inner surface of the membrane forming a wall of the fluid chamber such that a portion of the fluid chamber is positioned proximal to the proximal lumen opening, wherein the depressable exposed portion of the membrane is configured to depress distally into a depressed position when pressed by a finger, the depressing of the depressable exposed portion into the depressed position reducing a volume of the fluid chamber thereby causing the blood within the fluid chamber to be expelled through the distal lumen opening.

2. The vent plug of claim 1, wherein a portion of the outer surface of the membrane is coupled to the proximal terminal end of the body and extends distally into the lumen beyond the proximal lumen opening and couples to a surface of the lumen.

3. The vent plug of claim 1, wherein the membrane is configured to depress distally to expel a volume of blood of at least 0.05 mL from the fluid chamber.

4. The vent plug of claim 1, wherein the distal lumen opening has an inner perimeter equal to or less than 2.0 mm.

5. The vent plug of claim 1, wherein the distal lumen opening is circular and has a diameter between 0.1 mm to 0.6 mm.

6. The vent plug of claim 1, wherein the distal lumen opening is circular and has a diameter between 0.2 mm to 0.3 mm.

7. The vent plug of claim 1, wherein the fluid chamber has a volume of at least 0.1 mL.

8. A vent plug comprising:
   a body having a distal terminal end, a proximal terminal end, and a lumen extending through the distal and proximal terminal ends to form a distal lumen opening and a proximal lumen opening; and
   a membrane disposed across an entire width of the lumen, the membrane configured to prevent passage of blood through the lumen, the membrane being hydrophobic and air permeable, the membrane dividing the lumen into an air chamber proximal the membrane and a fluid chamber distal the membrane for collecting the blood, wherein an inner surface of the fluid chamber tapers inwardly along a portion of the inner surface from the membrane to the distal lumen opening;
   the distal lumen opening being shaped and sized to retain the blood within the fluid chamber until a change in an internal pressure of the lumen occurs, wherein a portion of the body that is proximal to the membrane is configured with an accordion shape comprising a first series of adjacent depressable indents formed into an inner surface of the portion of the body and a second series of adjacent depressable indents formed into an outer surface of the portion of the body, the first and second series of adjacent depressable indents configured to depress when a distal force is applied to the proximal terminal end of the body, the first series of adjacent depressable indents being parallel to the second series of adjacent depressable indents, the proximal lumen opening comprising an elastomeric material configured to form a seal against a human finger when the human finger is pressed against the proximal terminal end of the body to apply the distal force to collapse the portion of the body towards the membrane, formation of the seal combined with collapsing of the portion of the body causing the change in the internal pressure of the lumen thereby causing the blood to be expelled from the fluid chamber, the seal sealing the proximal lumen opening.

9. The vent plug of claim 8, wherein the distal lumen opening has an inner perimeter equal to or less than 2.0 mm.

10. The vent plug of claim 8, wherein the distal lumen opening is circular and has a diameter between 0.1 mm to 0.6 mm.

11. The vent plug of claim 8, wherein the distal lumen opening is circular and has a diameter between 0.2 mm to 0.3 mm.

12. The vent plug of claim 8, wherein the fluid chamber has a volume of at least 0.1 mL.

13. A method for collecting a blood sample using a vent plug, the method comprising:
   collecting blood within the vent plug disposed within a port of an intravenous infusion therapy system, the vent plug comprising:
      a body having a distal terminal end, a proximal terminal end, and a lumen extending from the distal terminal end to the proximal terminal end to form a distal lumen opening at the distal terminal end and a proximal lumen opening at the proximal terminal end;
      a membrane having an inner surface and an outer surface, the membrane being disposed at the proximal terminal end of the body and continuously across an entire width of the proximal lumen opening of the lumen, the membrane configured to prevent passage of the blood through the membrane, the membrane being hydrophobic and air permeable, the membrane coupled to the proximal terminal end of the body, the membrane comprising a depressable exposed portion that is biased to bulge proximally out from the proximal lumen opening such that a portion of the inner surface of the membrane is positioned proximal to the proximal lumen opening; and
      a fluid chamber formed within the lumen distal the membrane for collecting the blood, the inner surface of the membrane forming a wall of the fluid chamber such that a portion of the fluid chamber is positioned proximal to the proximal lumen opening;
   removing the vent plug from the intravenous infusion therapy system; and
   expelling a volume of the blood from the vent plug by depressing the depressable exposed portion into a depressed position thereby reducing the volume of the blood.

14. The method of claim 13, wherein a portion of the outer surface of the membrane is coupled to the proximal terminal end of the body and extends distally into the lumen and couples to a surface of the lumen.

* * * * *